United States Patent [19]

Fusco et al.

[11] Patent Number: 4,956,460
[45] Date of Patent: Sep. 11, 1990

[54] PROCESS FOR THE PREPARATION OF 1-ALKYL-3-CARBOXY-4-CINNOLONES

[75] Inventors: Raffaello Fusco; Fulvio L. Piselli; Pier M. Boschi, all of Milan, Italy

[73] Assignee: Industria Chimica Profarmaco S.P.A., Milan, Italy

[21] Appl. No.: 172,072

[22] Filed: Mar. 23, 1988

[30] Foreign Application Priority Data

Apr. 23, 1987 [IT] Italy ................... 20230 A/87

[51] Int. Cl.$^5$ ............... C07D 237/28; C07D 491/056
[52] U.S. Cl. ............................ 544/234; 544/235; 549/439; 560/34; 562/439; 562/868
[58] Field of Search ........................... 544/234, 235

[56] References Cited

U.S. PATENT DOCUMENTS

| 2,797,218 | 6/1957 | Barber et al. | 544/235 |
| 3,485,845 | 12/1969 | Davis et al. | 546/153 |
| 3,669,965 | 6/1972 | White | 544/234 |
| 3,937,704 | 2/1976 | Stranotmann et al. | 544/235 |
| 4,495,351 | 1/1985 | Schmidt et al. | 544/234 |

FOREIGN PATENT DOCUMENTS

| 138661 | 4/1985 | European Pat. Off. | 544/235 |
| 144264 | 9/1982 | Japan | 544/235 |

OTHER PUBLICATIONS

"Advanced Organic Chemistry" by Jerry March (3rd. Ed.) p. 485 (1985).
Comprehensive Heterocyclic Chemistry, vol. 3, Part 2B, pp. 42-43, "The Structure, Reactions, Synthesis and Uses of Heterocylic Compounds", Pergamon Press (1984).

Primary Examiner—Mukund J. Shah
Assistant Examiner—E. Bernhardt
Attorney, Agent, or Firm—Walter H. Schneider

[57] ABSTRACT

A process for the preparation of 1-alkyl-3-carboxy-4-cinnolones of formula I

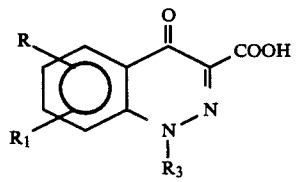

wherein R and $R_1$ are electron donor groups and $R_3$ is an alkyl group, starting from an amine of formula II

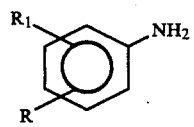

which is subjected to the following transformations;
(1) diazotation;
(2) coupling with a cyanoacetic ester;
(3) alkylation of the arylhydrazone obtained in (2);
(4) hydrolysis of the ester and conversion into acyl chloride;
(5) intramolecular cyclization;
(6) hydrolysis of the nitrile residue.

6 Claims, No Drawings

PROCESS FOR THE PREPARATION OF 1-ALKYL-3-CARBOXY-4-CINNOLONES

The present invention relates to a process for the preparation of 1-alkyl-3-carboxy-4-cinnolones of formula I

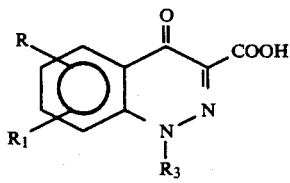

wherein R and $R_1$, which may be the same or different, are hydrogen or electron donor groups such as alkoxy or alkylthio groups, or, taken together, are a methylenedioxy group; $R_3$ is a $C_1-C_6$ alkyl group.

The invention also relates to novel intermediates useful for the preparation of compounds I.

Compounds of formula I, particularly 1-ethyl-3-carboxy-6,7-methylenedioxy-4-cinnolone (Formula I, wherein $R = R_1 =$ -methylenedioxy, $R_3 =$ -ethyl), are known therapeutic agents having antibacterial activity.

The processes hitherto known (DE-2005104) suffer from some drawbacks such as the use of toxic and dangerous reactants (bromine, cyanides) and the formation of by-products which are difficult to be removed, with a consequent decrease in the yields.

The process according to the invention allows to overcome the drawbacks of the prior art, said process being characterized by few steps, high yields and use of reactants which are not particularly dangerous.

The process according to the invention is summarized in the following scheme.

Compounds of formulae III, IV, V and VI are novel and thus form a further object of the invention.

Arylazocyanoacetic esters III are prepared according to known methods, by coupling the diazo-compound of an arylamine II with a cyanoacetic acid ester. Subsequent alkylation of esters III is carried out with alkylating agents $R_3X$, wherein $R_3$ has the above mentioned meanings and X is an halogen atom or a sulfate residue, in a preferably polar aprotic solvent and in the presence of bases. Alkali carbonates, such as $K_2CO_3$ or $Na_2CO_3$ are used as bases, while appropriate solvents are lower aliphatic ketones, dimethylformamide, methylpyrrolidone, acetonitrile.

The reaction temperatures range from 10° to 100° C., preferably from 30° to 40° C., for the times necessary to complete the reaction.

It is often appropriate to use an excess of the alkylating agent, whether the alkylation conditions may involve, as a side reaction, hydrolysis of a part of the alkylating agent itself.

Hydrolysis of compound IV to give compounds V is effected using (in stoichiometric ratios) an alkali hydroxide such as NaOH or KOH, in the presence of a water-miscible solvent such as an alcohol, at temperatures from 0° to 80° C., preferably 20° to 30°, for time sufficient for the hydrolysis to be completed.

Any small amount of carbon-alkylated products (arylazo-alkyl-cyanoacetic esters) are not hydrolyzed in the selected conditions and can be removed before acidification, since they are not water-soluble.

Acids V are then transformed into corresponding acyl chlorides VI by reaction with a chlorinating agent such as $SOCl_2$, $PCl_3$, $PCl_5$ in such appropriates solvents as benzene, toluene, chloroform, methylene chloride, chlorobenzene, usually working under reflux until gas evolution is over.

Intramolecular cyclization of compounds VII is sur-

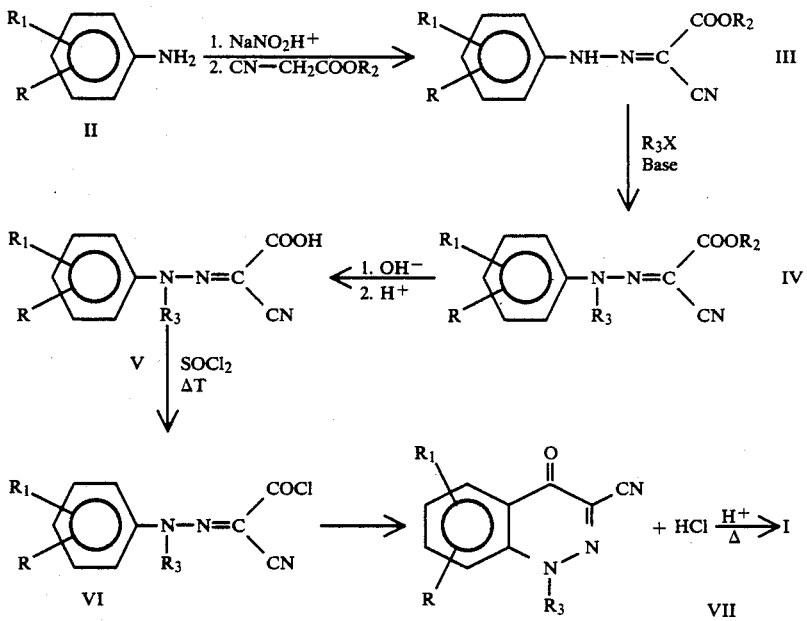

In the above formulae, R and $R_1$ have the above mentioned meanings, $R_2$ is $C_1-C_4$ straight or branched alkyl group and $R_3$ is a $C_1-C_6$ straight or branched alkyl group or a $C_3-C_6$ cycloalkyl group.

prisingly carried out by simple heating, in the absence of Lewis acids, for instance by refluxing the acyl chloride in an appropriate inert solvent, at a temperature ranging from 100° to 150° C., until HCl evolution is over.

Under such conditions, yield are high and formation of resinous by-products is not observed. In case substituents R and $R_1$ on the ring are electron donors enough, e.g. for the methylenedioxy residue, chlorination of acids V and subsequent cyclization may be carried out in a single step, by suitably selecting the solvent.

Conversion of nitrile into the final product is eventually effected by acid hydrolysis, according to known methods.

The following non limiting examples further illustrate the invention.

EXAMPLE 1

Ethyl 3,4-methylenedioxyphenylazocyanoacetate 3.1 kg of 3,4-methylenedioxyaniline hydrochloride were dissolved in 9 of water +3 l of conc. HCl. A solution of 1.32 kg of $NaNO_2$ in 4 l of water was slowly added, cooling to 0° C. in outer bath.

The resulting diazo solution was added under stirring, during 1 hour 30, again at 0° C., to a solution obtained mixing 1.3 l of water, 2.7 l of acetic acid, 4 l of 30% (w/w) NaOH, 9 l of ethanol and 2.31 kg of ethyl cyanoacetate. Temperature was left to gradually rise to 15° C. during 2 hours, then the precipitate was filtered and washed twice with 15 ml of ethanol at 0° C.

Yield: 90% on theor.; m.p. 115°–118° C.; orange product, which may be recrystallized from ethanol.

By the same procedure, using methyl cyanoacetate, the corresponding methyl ester was obtained, m.p. 177° C.

EXAMPLE 2

Ethyl 3,4-methylenedioxyphenyl-N'-ethyl-phenylhydrazonocyanoacetic 2.15 kg of dry powdered $K_2CO$ and 6.8 kg of diethyl sulfate were added to 4.35 kg of the thoroughly dried compound of example 1.

The mixture was refluxed for 5 hours with stirring, cooled to 20°, and the precipitate was filtered and washed twice with acetonitrile (2.5 l each time).

The filtrate was evaporated to dryness under vacuum and the residue was treated with 2 l of isopropanol. The mass was stirred for 1 hour and the crystals were filtered and washed 3 times with 0.5 l of isopropanol cooled to 0° C. 2.7 kg of the pure compound were obtained, m.p. 78°–80° C., of yellow colour, which can be recrystallized from ethanol.

By the same procedure, using the corresponding methyl ester, the corresponding ethylation compound was obtained, melting at 129°–131° C.

EXAMPLE 3

Acid 3,4-methylenedioxyphenyl-N'-ethyl-phenylhydrazonocyanoacetic acid acid.

1.84 kg of the ester prepared according to example 2 were suspended in 5.4 l of ethanol and 5.6 l of water and 6.3 l of 30% (w/w) of NaOH were added thereto. The mixture was stirred at room temperature for 20 hours, then ethanol was removed by concentration under reduced pressure. Upon acidification with HCl of the filtered solution, a product separated in form of a gum, which slowly solidified. The crude filtrate was ground and washed with some ethyl cyanoacetate.

Yield: 1.5 kg of product, which was purified by dissolution in diluted alkali, filtration with charcoal and reprecipitation with acetic acid. Yellow product, m.p. 131°–133° C.

The same compound was obtained, according to the same procedure, from the corresponding methyl ester.

EXAMPLE 4

3,4-methylenedioxyphenyl-N'-ethyl-phenylhydrazonocyanoacetic acid chloride.

2 kg of thionyl chloride were added to 3 kg of the acid described in example 3, thoroughly dried and ground, suspended in 1,5 l of dichloroethane. The mixture was refluxed for 5 hours, then the solution added with some decolorizing carbon was filtered and left to crystallize overnight at 0° C. The separated acyl chloride was filtered. Some more product was recovered by filtration of mother liquors. 2.4 kg of compound were obtained, m.p. 170° C. with decomposition (75% on theor.).

EXAMPLE 5

1-ethyl-3-cyano-methylenedioxy-4-cinnolone 7.5 kg of acyl chloride, prepared according to example 4, were suspended in 10 l of chlorobenzene and taken to ebullition under stirring, refluxed for 6 hours, then cooled to 0° C. for 3 hours.

Crystals were filtered and washed with some methylene chloride.

5.5 kg of compound were obtained, unitary by TLC, (m.p. 265° C.), which was colorless and poorly soluble in common solvents.

Alkali hydrolysis of this nitrile, according to the method already described in literature, gives the corresponding acid.

EXAMPLE 6

1-ethyl-3-cyano-6,7-methylenedioxy-4-cinnolone 75 kg of the compound prepared as described in example 3, thoroughly dried, were suspended into 1000 l of chlorobenzene. 52 kg of thionyl chloride were added to the suspension, which was gradually heated to reflux to 80° C., keeping this temperature for about 10 hours.

A partial vacuum was then applied and 750 l of chlorobenzene were distilled at about 50°–80° C.; then vacuum was interrupted and the solution was refluxed (about 135° C.) for about 6 hours. The solution was then cooled to 0° C., the separated solid was filtered and washed twice in centrifuge with 50 l each time of methylene chloride.

The solid was ground with 300 ml of methylene chloride under stirring for 30 min., refiltered and dried.

Yield: 54 kg (79%) of compound, unitary in TLC.

We claim:

1. A process for the preparation of a cinnolone of formula I

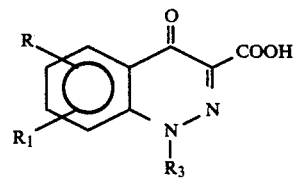

wherein R and $R_1$, which may be the same or different, are hydrogen, alkoxy, alkylthio or, taken together, are methylenedioxy $R_3$ is $C_1$-$C_6$ alkyl or $C_3$-$C_6$ cycloalkyl which process comprises;

(a) diazotization of a compound of formula II

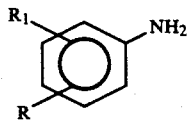

wherein R and $R_1$ are as above defined with an alkali nitrite in an acid medium suitable for diazotrization, followed by reaction with a cyanoacetric acid ester of formula $CN-CH_2-COOR_2$ ($R_2=C_1$-$C_4$ alkyl), to give a compound of formula III

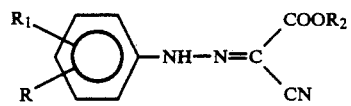

(b) alkylation of the compound of formula III with an alkylating agent $R_3X$ (X=halogen or sulfate and $R_3$ is the same as defined above in the presence of a base selected from alkali hydroxides and carbonates and a polar aprotic solvent at a temperature of 10°-100° C. to give an ester of formula IV

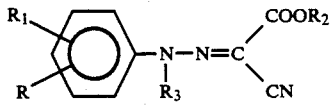

(c) hydrolysis of the ester of formula IV to carboxylic acid with an alkali hydroxide in a water miscible solvent at a temperature of 0°-80° C., chlorination of the carboxylic acid to acyl chloride with a chlorinating agent in an inert solvent, and intramolecular cyclization of the acyl chloride in an inert solvent at a temperature of 100°-150° C. and in the absence of catalyst to give a compound of formula VII

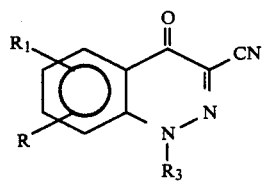

and (d) acid hydrolysis of the compound of formula VII to the compound of formula I.

2. A process according to claim 1, wherein R and $R_1$, taken together, form a methylenedioxy ring.

3. A process according to claim 1, wherein $R_2$ is $CH_3$ or $C_2H_5$.

4. A process according to claim 1 wherein $R_3$ is $C_2H_5$ and X is sulfate.

5. A process according to claim 1 in which formula I is 1-ethyl-3-carboxy-6,7-methylenedioxy-4-cinnolone.

6. A process according to claim 2 in which the chlorination of the carboxylic acid and intramolecular cyclization of the acyl chloride are conducted as a single step.

* * * * *